US00PP37059P2

(12) United States Plant Patent
Hansen

(10) Patent No.: US PP37,059 P2
(45) Date of Patent: Oct. 21, 2025

(54) ***PANICUM* PLANT NAMED 'Half Pint'**

(50) Latin Name: ***Panicum virgatum* (L.)**
Varietal Denomination: Half Pint

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,465

(22) Filed: Jan. 29, 2025

(51) Int. Cl.
*A01H 5/12* (2018.01)
*A01H 6/46* (2018.01)

(52) U.S. Cl.
USPC ..... Plt./374
CPC ..... *A01H 6/4642* (2018.05)

(58) Field of Classification Search
USPC ..... Plt./374
CPC ..... A01H 5/12
See application file for complete search history.

*Primary Examiner* — Kent L Bell

(57) ABSTRACT

A new and distinct plant of ornamental Switch Grass named *Panicum* 'Half Pint' with upright blue-green foliage that retains its coloration into the fall. The upright, compact, and dense culms produce small-height plants with broadly airy panicles beginning greyed green, developing rosy-reddish seed heads that are retained as creamy-tan into winter. The upright foliage and inflorescences produce a tight habit that is narrower than the height of the inflorescences. The new plant is useful in the landscape as a specimen, en masse, or in a container.

2 Drawing Sheets

Latin botanical classification: *Panicum virgatum* (L.).
Variety denomination: 'Half Pint'.

STATEMENT REGARDING PRIOR DISCLOSURES UNDER 37 CFR 1.77(B)(6)

The first disclosure of the claimed plant was the photograph and brief description on a website operated by Walters Gardens, Inc. on Feb. 1, 2024. The claimed plant was first offered for sale on Feb. 1, 2024, by Walters Gardens, Inc. to In the Country Garden and Gifts. Walters Gardens, Inc. obtained the plant and all information relating thereto, from the inventor. No plants of *Panicum* 'Half Pint' have been sold anywhere in the world nor has any disclosure of the new plant been made more than one year prior to the filing date of this application, and such sale or disclosure within one year was either derived directly or indirectly from the inventor and would be a 35 U.S.C. 102(b) exception.

BACKGROUND OF THE PLANT

*Panicum* 'Half Pint', hereinafter also referred to by the cultivar name 'Half Pint' and the "new plant" is a new and distinct cultivar of Switch Grass.

The new plant originated from a self-pollination of 'Apache Rose' U.S. Plant Pat. No. 29,142 at a wholesale perennial nursery in Zeeland, Michigan in the late summer of 2014. The seed was collected on Oct. 13, 2014, and was sown the following spring. The individual seedling was initially selected from among many for further observation in the summer and fall of 2016 at which time it was assigned the breeder code 14-5-11 before assigning the new plant cultivar name 'Half Pint'.

The new plant has been successfully asexually propagated by division since late fall of 2016 at the same wholesale perennial plant nursery in Zeeland, MI, and found to produce stable and identical plants that maintain the unique characteristics of the original plant. The plant is stable and reproduces true-to-type in successive generations of asexual reproduction.

BRIEF SUMMARY OF THE PLANT

*Panicum* 'Half Pint' differs from its female parent, 'Apache Rose', in that the new plant is shorter, with more upright foliage, and has more blue-green foliage that does not change over the growing season.

The nearest comparison varieties known to the inventor are: 'Apache Rose' U.S. Plant Pat. No. 29,142, 'Gunsmoke' U.S. Plant Pat. No. 32,373, 'Niagara Falls' U.S. Plant Pat. No. 34,509, and 'Prairie Fire' U.S. Plant Pat. No. 19,367.

'Gunsmoke' has a taller habit and has more arching foliage. 'Niagara Falls' is taller with more upright leaves and the foliage produces a broader, larger, more-defined, and arching skirt. 'Prairie Fire' has a slightly taller and more arching habit, the culms are looser and not as densely arranged, and the foliage develops a deep wine color in the summer.

Table 1 below includes comparisons of other *Panicum* cultivars known to the inventor:

TABLE 1

| CULTIVAR | U.S. PLANT Pat. No. | TOTAL HEIGHT in CM | INITIAL FOLIAGE COLOR |
|---|---|---|---|
| 'Apache Rose' | PP29,142 | 95 | gray-green |
| 'Cape Breeze' | PP24,895 | 75 | dark green |
| 'Cheyenne Sky' | PP29,209 | 112 | blue-green |

TABLE 1-continued

| | | | |
|---|---|---|---|
| 'Gunsmoke' | PP32,373 | 135 | blue-green |
| 'Haense Herms' | (not patented) | 100 | green |
| 'Half Pint' | current application | 90 | blue-green |
| 'Hot Rod' | PP26,074 | 90 | blue-green |
| 'Niagara Falls' | PP34,509 | 108 | blue-green |
| 'Prairie Fire' | PP19,367 | 100 | blue-green |
| 'Rostrahlbush' | (not patented) | 110 | green |
| 'RR1' | PP17,994 | 120 | blue-green |
| 'Shenandoah' | (not patented) | 140 | blue-green |

| CULTIVAR | SEASONAL FOLIAGE COLOR | SEASON OF CHANGE BEGINNING | HABIT |
|---|---|---|---|
| 'Apache Rose' | purple-tipped | late July | dense upright |
| 'Cape Breeze' | purple-tipped | late September | broadly upright |
| 'Cheyenne Sky' | concord purple | early July | very upright |
| 'Gunsmoke' | blue-green | none | upright arching |
| 'Haense Herms' | red-purple | early August | upright |
| 'Half Pint' | blue-green | none | upright |
| 'Hot Rod' | red-purple | early spring | upright |
| 'Niagara Falls' | blue-green | none | upright |
| 'Prairie Fire' | deep wine | early July | upright |
| 'Rostrahlbush' | red-purple | early August | upright |
| 'RR1' | purple-red | early July | compact |
| 'Shenandoah' | red-purple | late July | arching |

The new plant has a more upright and compact habit than all of the cultivars known to the inventor in the above Table 1.

The following traits of *Panicum* 'Half Pint', in combination, have been repeatedly observed in multiple generations of asexually propagated plants and distinguish the new plant from all other Switch Grass plants known to the inventor:

1. Blue-green foliage that retains its coloration into the fall;
2. Upright, compact, and dense culms producing small height plants that do not lodge;
3. Foliage and inflorescences are narrower than the height;
4. Broadly airy panicles beginning greyed green, developing rosy-reddish seed heads that are retained as creamy-tan into winter.

BRIEF DESCRIPTION OF THE DRAWINGS

The photographs of the new plant demonstrate the overall appearance of a six-year-old plant growing in an outdoor display garden in Zeeland, MI, including the unique traits. The colors are as accurate as reasonably possible with color reproductions. Ambient light spectrum, source, and direction may cause the appearance of minor variation in color.

DETAILED BOTANICAL DESCRIPTION

Figure 1:
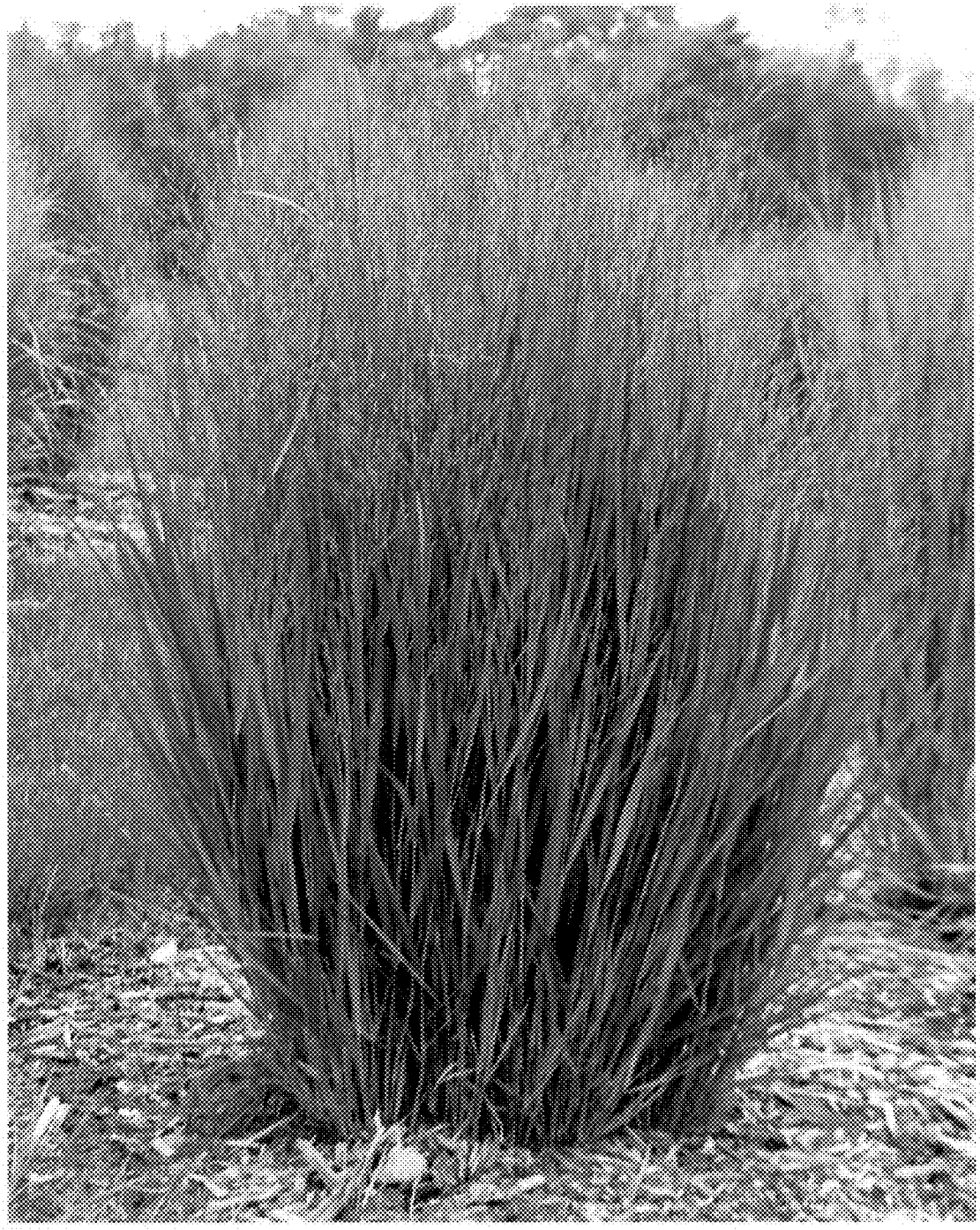
FIG. 1 shows the overall plant in mid-season.
Figure 2:
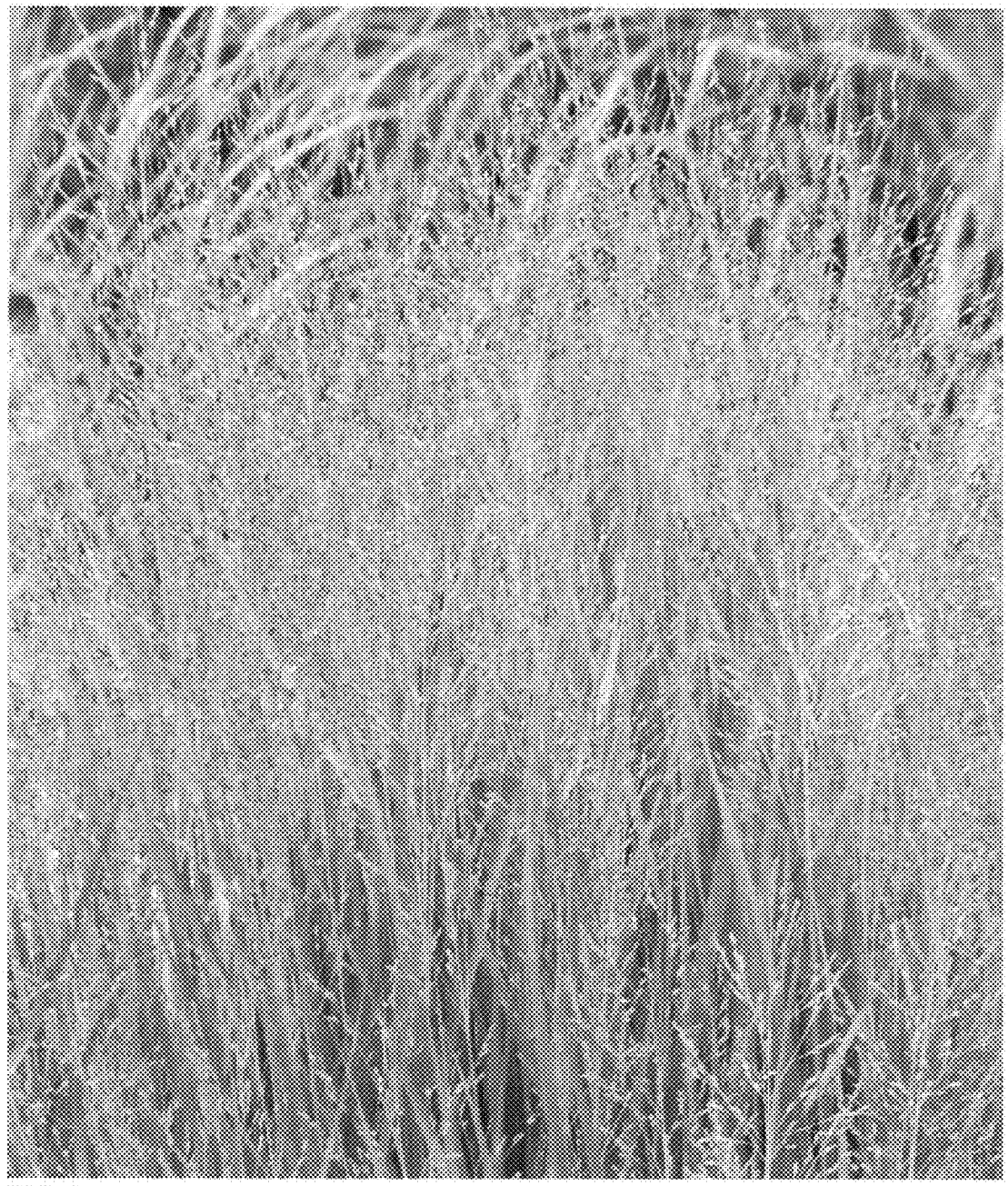
FIG. 2 shows a close-up of the inflorescence in late summer.

The following descriptions and color references are based on the 2015 edition of The Royal Horticultural Society Colour Chart except where common dictionary terms are used. 'Half Pint' has not been observed in all possible environments. The phenotype may vary slightly with different environmental conditions, such as temperature, light, fertility, moisture, and maturity levels, but without any change in the genotype. The following observations and descriptions are of a two-year-old and four-year-old plant in a full-sun loamy-sand field and loamy-sand trial garden, respectively, of a wholesale perennial nursery in Zeeland, Michigan, USA, grown in with supplemental water and fertilizer as needed.

Parentage: Female (seed parent) 'Apache Rose';

Propagation method: By division of the culms;

Growth rate: Moderately vigorous;

Time to finishing in a 3.8-liter pot: About 10 to 12 weeks from 25 mm diameter plug; Rooting habit: normal, coarsely branching; root color nearest RHS 155D depending on soil matrix;

Plant shape and habit: Winter-hardy, herbaceous, rhizomatous perennial forming compact upright culms with upright foliage, topped with finely-textured airy inflorescence producing a broad clump that is taller than it is wide;

Plant size: Four-year-old plants to 90 cm tall, 72 cm wide about 45 cm above soil, and 41 cm wide at base; field grown two-year-old plants to about 75 cm tall at flowering time, about 20 cm wide at the soil line and about 38 cm at the widest point about 35 cm above the soil;

Foliage description: Glabrous, glaucous; linear; flat; margin with microscopic marginal dentations; sheathed slightly less than the node of attachment to ligule, adaxial and abaxial surfaces dull; strongly upright; deciduous but persist through winter;

Foliage size: To about 49 cm long and to about 11 mm wide and to about 38 cm long without sheath; averaging with sheath about 42 cm long and 9.5 mm wide; shorter at the proximal end; typically 4 leaves per culm;

Foliage color: Adaxial and abaxial more grey than RHS NN137A and RHS 189A; winter adaxial surface more grey than RHS 164D; winter abaxial surface between RHS 199D and RHS 164D;

Veins: Parallel; midrib about 0.5 mm across; adaxial slightly recessed, abaxial slightly ridged;

Vein color: Adaxial midrib in proximal 5 to 7 cm nearest RHS 191C, adaxial secondary veins and abaxial midribs and secondary veins indistinguishable and same color as surrounding leaf;

Culm: Erect; terete, hollow; glabrous; glaucous; dull surface; about 75% enclosed by leaf sheath; about 400 culms per four-year-old clump and 80 per two-year-old clump;

Culm dimension: To about 53 cm long without panicle, average about 46 cm; to about 3.5 mm diameter at base and 5 mm across at lower nodes; internode length average about 10 cm, shorter proximally;

Culm color: Variable; proximally under sheath nearest RHS 146D; mid-section nearest RHS 138A without glaucous bloom, and with glaucous bloom nearest RHS N138C and RHS 189B; distal portion nearest RHS 138A;

Node description: About 4 per culm, swollen to about 5 mm diameter;

Node color: Variable; proximally nearest RHS 200B, distally nearest RHS 165C;

Ligule: Sparse; less than 1 mm long and 4 mm wide; color nearest RHS 160D;

Inflorescence description: Finely-branched open panicle, one panicle per culm;

Inflorescence timing: Beginning late August, flowering into September, panicles dry and remain effective through winter;

No flower fragrance detected;

Panicle: Ellipsoidal with acute apex; to about 33 cm long and 12 cm wide near middle; overall effective color seasonally variable, nearest RHS 194B early in season; fall nearest RHS 195B with nearest RHS N187A in distal portion of lemma and palea; winter drying to nearest RHS 161D;

Pedicel: Cylindrical; glabrous; fine and wiry; average about 4 mm long and 0.02 mm diameter; color nearest RHS 138B;

Rachis: Terete, branched, glabrous, glaucous; to about 30 cm long and about 2 mm diameter at base; branches to about 9 cm long and about 0.7 mm diameter held at about 60-degree angle above horizontal; color between RHS 138A and RHS N138B;

Spikelet: Usually with two florets; about 10 mm long and 2 mm wide;

Rachilla: Thin, terete, stiff; to about 9 mm long and about 0.2 mm diameter; color nearest RHS N138C;

Lower glume: Elliptical; convex; acute apex; about 3 mm long and 1 mm wide; without awn; color nearest RHS 138B;

Upper glume: Elliptical; convex; acute apex; about 3.5 mm long and 1 mm wide; without awn; color nearest RHS 138B;

Lower and upper glume: Elliptical; convex; acute apex; attenuate base; entire margins; smooth both adaxial and abaxial;

Lemma: Two; elliptical; convex; without awn; acute apex, truncate base; margin entire; upper and lower each about 3 mm long and 0.5 mm wide; color between RHS 139D and RHS 160D;

Palea: Ovate; acute apex, truncate base, margin entire; about 2 mm long and 0.7 mm across; translucent, nearest RHS 160D;

Gynoecium: Two;

*Stigma*.—Two, plumose, protruding about 1.5 mm from glume and about 0.5 mm diameter; color nearest RHS 165A.

*Style*.—Thin; about 1 mm long and 0.1 mm diameter; color nearest RHS NN155A.

*Ovary*.—Ellipsoidal; acute apex, rounded base; about 2.5 mm long and 1 mm diameter; color nearest RHS 148B.

Androecium: Typically two;

*Filaments*.—Short; hair-like; up to 1 mm long and less than 0.1 mm diameter; color nearest RHS NN155D.

*Anthers*.—Two; dorsifixed, longitudinal; about 2.5 mm long and about 1 mm wide; color nearest RHS N163A.

*Pollen*.—Abundant; less than 0.1 mm in diameter; nearly transparent, color lighter than RHS 155D.

Fruit: Caryopsis; about 2 mm long and about 1 mm wide; color between RHS 161D and RHS 199D;

Hardiness: At least from USDA zone 4 through 9;

Growth: The new plant is very drought once established and the stems are resistant to lodging;

Disease and pest resistance or susceptibility: 'Half Pint' has not shown any disease resistance or susceptibility greater than or less than typical *Panicum* known to the inventor, including moderate susceptibility for *Puccinia* sp.

I claim:

1. A new and distinct cultivar of ornamental Switch Grass, *Panicum* plant named 'Half Pint', as herein described and illustrated.

* * * * *